United States Patent [19]

Eldridge, Jr. et al.

[11] 4,395,807
[45] * Aug. 2, 1983

[54] SURGICAL BLADE REMOVER

[75] Inventors: John D. Eldridge, Jr., Newport Beach; Milton W. Cohen, Orange, both of Calif.

[73] Assignee: Instranetics, Inc., Tustin, Calif.

[*] Notice: The portion of the term of this patent subsequent to Aug. 17, 1999, has been disclaimed.

[21] Appl. No.: 290,361

[22] Filed: Aug. 5, 1981

[51] Int. Cl.³ ............................................. B23P 19/04
[52] U.S. Cl. .................................... 29/239; 29/278; 206/355; 206/359
[58] Field of Search ................. 29/278, 239; 30/339; 206/349, 355, 359; 81/3 R

[56] References Cited

U.S. PATENT DOCUMENTS

| | | | |
|---|---|---|---|
| 3,172,316 | 3/1965 | Grieshaber | 81/3 R |
| 4,168,777 | 9/1979 | Gaskell et al. | 206/359 |
| 4,270,416 | 6/1981 | Thompson | 206/359 |
| 4,344,532 | 8/1982 | Eldridge, Jr. et al. | 206/355 |

Primary Examiner—James L. Jones, Jr.
Assistant Examiner—Steven P. Schad
Attorney, Agent, or Firm—Knobbe, Martens

[57] ABSTRACT

A surgical blade remover is disclosed wherein a surgical blade is easily and effectively removed from the tang of a handle. The device is provided with two members which are spaced to form a channel sized to permit the tang to be positioned between them while the blade rests on the upper surfaces of the members. The channel between the members at their lower portions widens to permit the handle to enter the channel sufficiently that the heel of the blade can abut a projection which extends upward from each surface of the members. The handle enters this widened lower portion of the channel while the blade rests against the upper surfaces of the members thereby releasing the heel of the blade from the tang. The blade can then be removed from the handle by pulling the handle out of the channel because the projections prevent the blade from moving with the handle.

5 Claims, 19 Drawing Figures

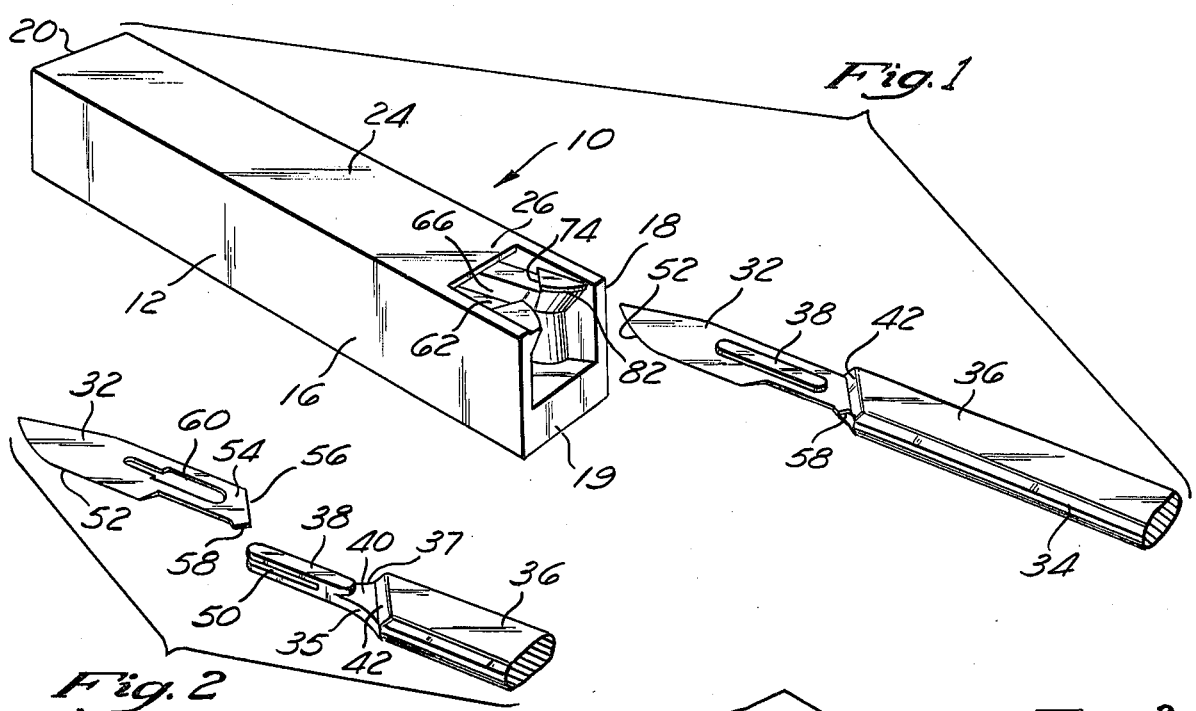

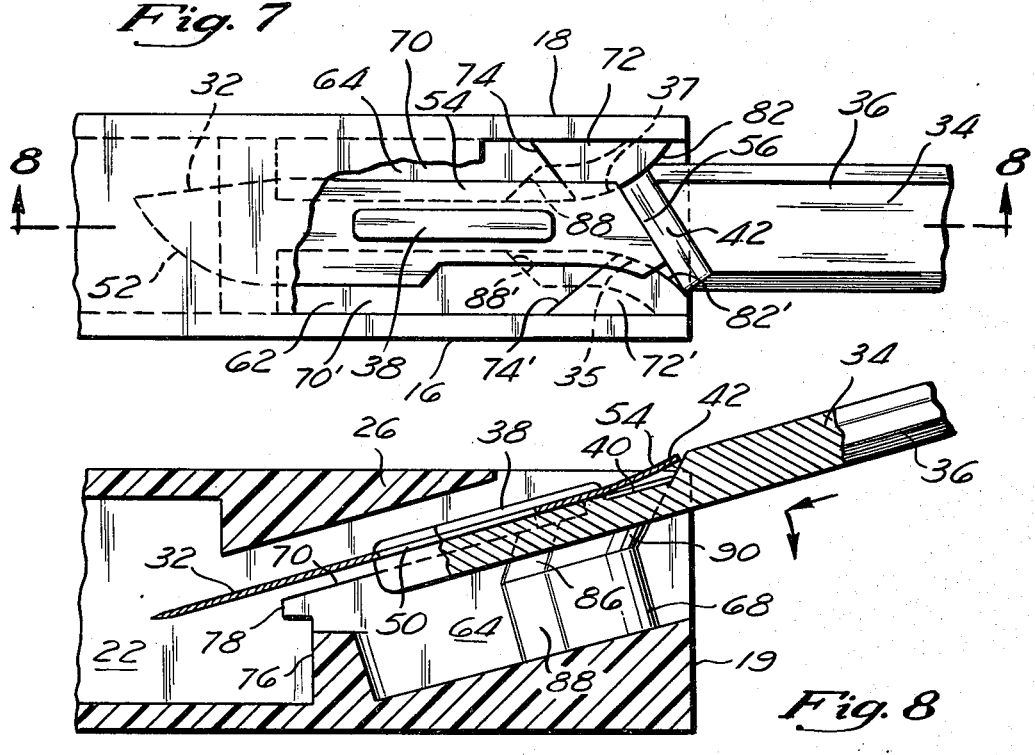
Fig. 7
Fig. 8
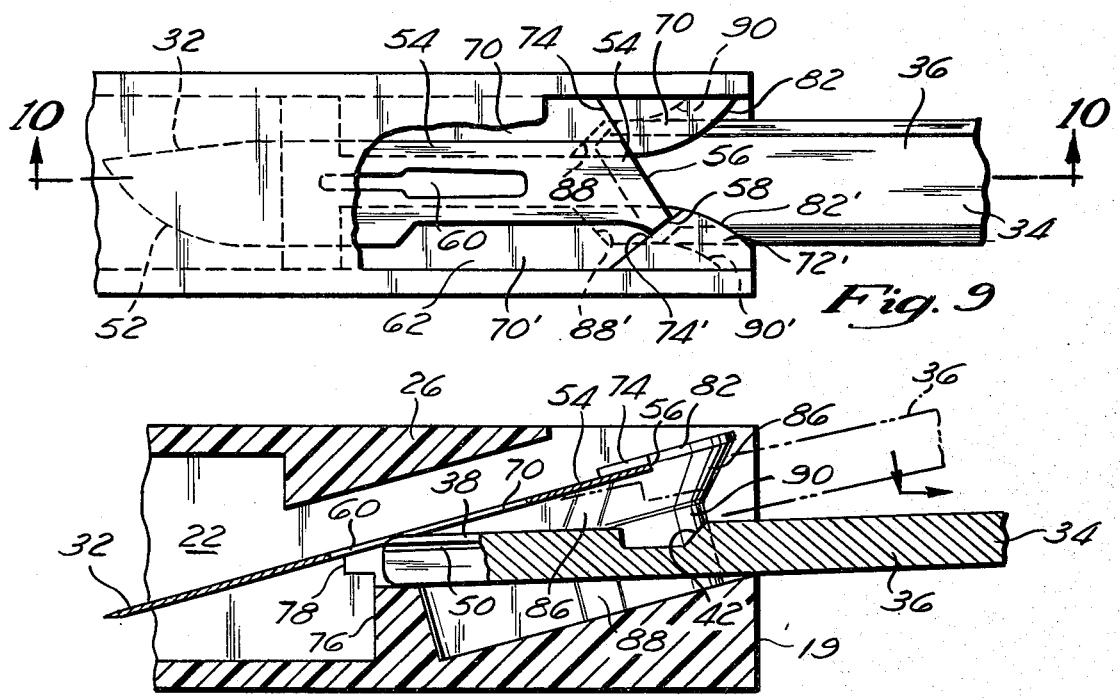
Fig. 9
Fig. 10

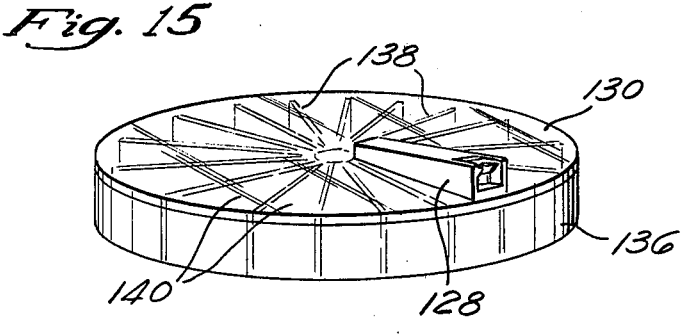
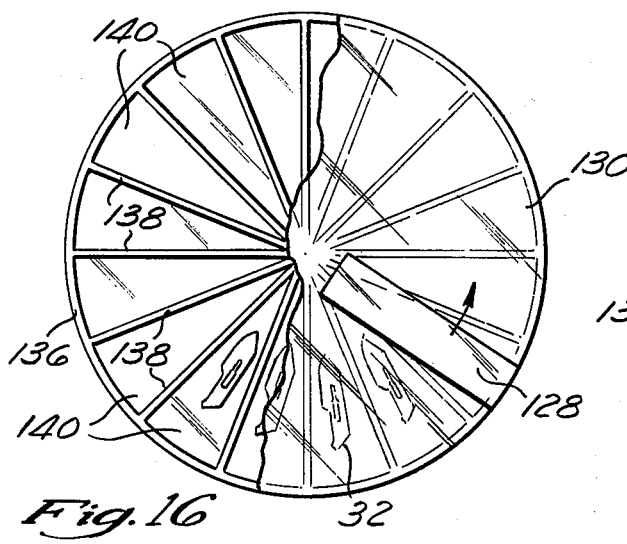
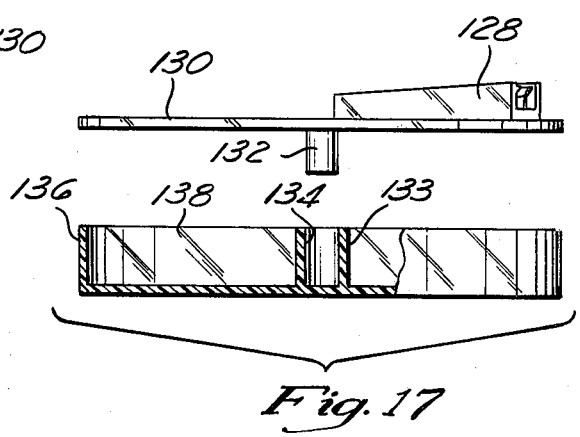
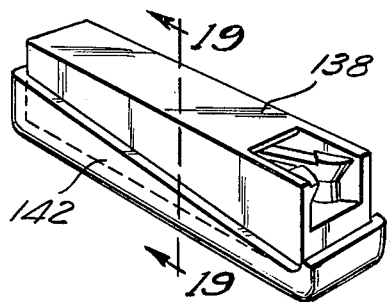
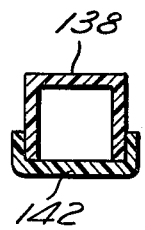

SURGICAL BLADE REMOVER

BACKGROUND OF THE INVENTION

The invention is directed toward devices for removing surgical blades from blade holders.

The scalpel, as a surgical implement, typically includes a handle having a tang with an upraised portion that mounts a replaceable blade. The handle, which can be resterilized, and is therefore reusable, is typically produced in one of two sizes, i.e. No. 3 and No. 4. The tang of a No. 3 handle is of a standard size to fill all sizes of the smaller dissecting blades used for internal incisions. Similarly, the tang of a No. 4 handle is of a standard size to fit all sizes of skin blades which are used to sever the skin in the initial incision. The width of the heel of each of these surgical blades is fairly standard.

Each blade has a longitudinal opening cut therethrough which is adapted to slidably accommodate the upraised portion of the tang. When the tang is slidably positioned to project through the opening in the blade, the spring steel of the blade allows it to snap over the projection of the tang, locking the blade on the handle.

The blades are not reusable, and therefore must be safely and efficiently removed from the reusable handle. In order to remove the blade, the rearward portion of the blade adjacent the opening, i.e., the heel, must be pried upward or distorted in order to clear the projection of the tang. In the past, the surgical nurse has often accomplished this task by using a forceps. With the heel portion of the blade pried over the top of the projection, the blade is then held by an instrument, such as a forceps, and is slidably pulled off the handle tang. Such manual removal of the soiled blade is not only awkward, but also can be hazardous since the blade may carry viruses or other infectious disease.

At the conclusion of surgery, it is also important that all blades used be accounted for and discarded in a package which will not permit removed blades to fall out.

U.S. Pat. No. 4,120,397, issued to Neumann, represents an attempt to devise a blade remover which has a downwardly extending projection that pushes the heel of the blade over the tang. When the handle is removed from the device, an inner wall abuts the heel of the blade and prevents the blade from following the handle. The device, while perhaps an improvement over the manual forceps method, is not satisfactory since it is awkward and frustrating to manipulate. Even after fully understanding how the device is to be used, the blades are removed with difficulty. Moreover, the construction of the device is expensive, cumbersome and bulky.

Another device is manufactured by Devon Industries, Inc., under the trademark "BladeGuard". The remover has an upright member with a square notch cut therein. A horizontal guard is located above and directly in front of the notched member. The tang is slid forward through the notch until only the heel portion of the blade rests on the member. The handle is then pressed downward which lifts the heel of the blade from the tang. The handle is then pulled out from the blade which is prevented from following by the guard. This device is also somewhat difficult to use and requires some operator dexterity in order to be able to remove blades efficiently.

A device similar to the Devon device in basic concept is manufactured by Jermed Limited. The device has a notched member which pries the heel of the blade over the tang when the handle is pressed upward. The handle is then pulled out from the blade which is prevented from following by an overhanging surface which catches the heel of the blade.

Each of these prior art devices requires a plurality of elements, one positioned on one side of the blade, that pries the blade over the tang and a second element, positioned on the opposite side of the blade, which abuts the heel of the blade to prevent the blade from moving with the handle as it is released.

There is therefore a definite need for a blade remover which easily and safely removes the blade, which is inexpensive and which is a self-contained unit that does not need elements positioned on each side of the blade for removal.

SUMMARY OF THE INVENTION

The inventive surgical blade remover has two members having proximal and distal ends spaced to form a channel. Each member has an upper blade receiving surface. The most proximal end of each of these surfaces has a projection which extends upwardly to form a shoulder. The distance between the members at their upper proximal ends is less than the distance between the members at their lower proximal ends. Thus, at their lower portions the members are undercut at about a 45° angle to form a wider channel. The 45° undercut is formed by a camming surface which extends between the upper and lower proximal ends of each member.

The handle and blade are initially inserted between the members in the upper narrower portion of the channel. In this portion the channel is wider than the tang but narrower than the blade to permit the tang to be inserted between the members while the blade rests on the blade receiving surfaces. As the handle is pushed toward the distal ends of the members the handle is automatically cammed downward along each camming surface. The camming surfaces therefore ensure that the handle will enter the lower portion of the channel. As this occurs, the heel of the blade is pried over the tang since the blade remains on the blade receiving surfaces while the handle is cammed downward. The wider portion of the channel is sized to permit the handle to be pushed toward the distal ends of the members until the heel of the blade clears the shoulders formed by the proximal projections on the blade receiving surfaces. When this occurs, the handle can be pulled longitudinally out of the device and the blade is removed because the heel of the blade abuts the shoulders and is prevented from following the handle.

The remover can be used with various types of containers that store the blades for disposal.

The device therefore permits the easy and quick removal of surgical blades without requiring hospital personnel to physically contact the blades themselves. The operator need only push the handle into the device, continue pushing until the handle is cammed downward and the heel of the blade clears the shoulders, and then pull the handle out. The device is a self-contained unit having only two complimentary contoured members which act on a single side of the blade for removal. Since the device is light weight and compact it is easy to manipulate and use and yet is economically disposable. Moreover, the device is capable of removing the various sizes of blades which are universally used.

DESCRIPTION OF THE PREFERRED EMBODIMENT

These and other advantages will be amplified and discussed below with reference to the following drawings in which:

FIG. 1 is a perspective view showing a handle and attached surgical blade ready for insertion into the blade remover device;

FIG. 2 is a perspective view showing a surgical blade detached from the neck of the handle;

FIG. 3 is an enlarged perspective view of the blade remover portion of the device;

FIG. 4 is a top view of the blade remover portion of the device;

FIG. 5 is a sectional view taken through line 5—5 of FIG. 4;

FIG. 6 is a sectional view taken through line 6—6 of FIG. 5.

FIG. 7 is a top view of a handle and attached blade when initially inserted into the remover;

FIG. 8 is a sectional view taken through line 8—8 of FIG. 7;

FIG. 9 is a top view of the handle and blade fully inserted into the remover;

FIG. 10 is a sectional view taken through line 10—10 of FIG. 9;

FIG. 15 is a perspective view of a fifth alternate embodiment;

FIG. 16 is a top view of the fifth alternate embodiment;

FIG. 17 is a side view partially in section showing the top detached from the base of the fifth alternate embodiment;

FIG. 18 is a perspective view of a sixth alternate embodiment;

FIG. 19 is a sectional view taken through 19—19 of FIG. 18.

DETAILED DESCRIPTION OF THE PREFERRED EMBODIMENT

Figure 11:
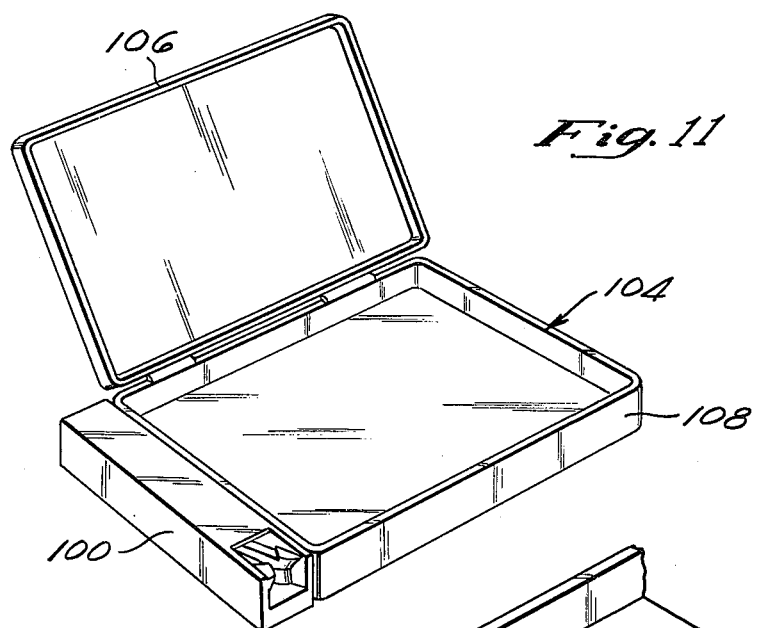
FIG. 11 is a perspective view of a first alternate embodiment.

Referring to FIGS. 1 and 5, a blade remover unit 10 is shown positioned within a front or proximal end of a generally rectangular container 12. The container 12 has left and right side walls 16, 18, and a base 19 which extend beyond the rear or distal end of the unit 10 to a back wall 20, forming a cavity 22 (shown in FIG. 5) behind the unit 10. The container 12 has a top 24 which covers the cavity 22 and the distal portion of the unit 10. Advantageously, the back wall 20 or other suitable section of the container 12 could be slidably removable to permit easy access to the cavity 22 by hospital personnel.

The container has an essentially open proximal end except that the base 19 slopes upward at about a 15° angle from the distal end of the unit 10 to the front of the container 12. As best shown in FIG. 5, since the unit 10 rests on the base 19, it also slopes upward at the same angle. This slope allows for an easier removal operation; however, is not required. As shown in FIG. 5, the proximal end 26 of the top 24 is essentially wedge shaped having a widened portion initiating slightly rearward of the distal end of the unit 10 that slopes upward at an angle essentially equal to the slope of the base 19 and the unit 10.

In a preferred embodiment, the dimensions of the container 12 are about 3½ inches long, by ⅝ inches wide, by ⅝ inches high. The container 12 is preferably made of a rigid, high impact resistant material. Advantageously, the material is clear to permit visual inspection of the contents of the cavity 22. Materials found satisfactory are clear acrylic plastic and polycarbonate.

As shown in FIG. 1, a blade 32 which is to be removed from its handle 34 is ready for insertion into the unit 10. The blade 32 is typically made of spring steel which provides it with some resiliency.

Referring to FIG. 2, the forward portion of the handle 34 is shown having a thicker body section 36, which gradually narrows by means of concavely curved left and right sides 35, 37 into a forwardly extending tang 38. At its junction with the tang 38, the upper side of the body section 36 has an angled surface 42 which slopes downward forming a recess 40 between the body 36 and an upwardly projecting portion of the tang 38. The forward most portion of the tang 38 has a longitudinal groove 50 which extends on each side of the tang 38 from its front edge back about ⅔ its length.

The blade 32 is shown having a forward cutting portion 52 and a rearward heel portion 54 which ends in a back edge 56 which is angled to abut the angled surface 42 of the handle 34. The heel portion 54 has a lateral edge 58 which is about ⅓ the length of the back edge 56 and which angles forwardly at about a 90° angle from the edge 56. The blade 32 has a centrally located opening 60 extending therethrough which narrows toward the front of the opening 60. It will be understood that the blade handle 34 and the blade 32, as described, do not form a part of the invention, and are well known in the art.

In order to mount the blade 32 on the blade handle 34, the groove 50 on the tang 38 slidably engages the edges of the opening 60. The tang 38 is then slidably moved with the aid of the groove 50, up to the forward most narrow portion of the opening 60. During this sliding process, the blade 32 is somewhat distorted from its planar configuration. As the upraised portion of the tang 38 begins to fit within the opening 60, the heel portion 54 of the blade 32 snaps down into recess 40. The blade 32 is thereby locked onto the handle 34 because the narrow portion of the opening 60 is narrower than the width of the tang 38. When the blade 32 is mounted, the back edge 56 of the blade 32 abuts the angled surface 42 of the handle 32. The complimentary contour of the back edge 56 and the angled surface 42 requires that when the blade 32 is correctly mounted, the cutting portion 52 will always be directed toward the left.

In order to remove the blade 32 from the handle 34, the heel 54 must be forced upward until it disengages from the tang 38. The blade 32 or the handle 34 are then slid relative to each other until the tang 38 is removed from the narrower portion of the opening 60. This frees the blade 32.

The features of the blade remover unit 10 will now be described with reference to FIGS. 3–6. The unit 10 has left and right members 62, 64 which extend inwardly from their respective sidewells 16, 18 and are mutually spaced forming a channel 66 therebetween. As used herein the term "inward" will means directed toward the channel 66 and "outward" will mean directed away.

Each member 62, 64 is preferably molded of the same material as the container 12. Because the left and right members 62, 64 are very similar in structure, the following description will be directed to the right member 64 which is more fully shown in FIG. 3. It will be understood that this description is applicable to either member unless an express differentiation is made. Moreover, the various portions of the left member 64 will be given the same reference numerals as the corresponding portions of the right member 62 except that a prime designation will be included.

Although the member 64 is an integral piece of material, it may be conceptualized as having an upper portion 66 and a lower portion 68. As best shown in FIG. 5, the upper portion 66 extends from a distal wall 76 forward to the proximal ends of the sidewall 18. This dimension will be referred to as the length of the member 64. The uppermost portion of the distal wall 76 has a distally extending flange 78.

The member 64 has an upper blade receiving surface 70, which at its most proximal end extends upwardly in a projection 72 forming a shoulder 74 with the remainder of the surface 70. As best shown in FIG. 4, the shoulder 74 angles outward from the sidewall 18 toward the front of the container 12 at about a 45° angle. Similarly the shoulder 74' of the left member 62 angles inwardly from the sidewall 16 toward the front of the container 12 at about a 45° angle.

As best shown in FIG. 5, the blade receiving surface 70 is essentially parallel to the base 19 which both angle upward at about a 15° angle at the proximal end of the container 12.

As best shown in FIGS. 3 and 4, the member 64 extends inwardly from the sidewall 18 to a vertical right side 80 which is essentially parallel to the sidewall 18. The distance between the right side 80 and the sidewall 18 will be referred to as the width of the member. The left member 62 has a corresponding left side 80'. The spacing between the left and right sides 80, 80' of the members 62, 64 at their distal ends is the narrowest portion of the channel 66 and is labeled $D_1$ in FIG. 4. The distance $D_1$ is greater than the width of the tang 38 but less than the width of the blade 32. This permits the tang 38 to be inserted within the narrower portion of the channel 66 between the members 62, 64 while the blade rests on the blade receiving surfaces, 70, 70'.

As best shown in FIGS. 3 and 4, the proximal end of the upper portion 66 of the member 64 has a section 82 which curves convexly outward from a point located at about the shoulder 74 until the member 64 meets the sidewall 18. The section 82 is curved to compliment the right curved side 37 of the tang 38 as will be understood in the discussion below. Similarly the member 62 has a curved section 82' which is curved to compliment the left curved side 35 of the tang 38.

The effect of the curved sections 82, 82' is to create a wider upper portion of the channel 66 at the proximal end of the unit 10 which is complimentary contoured to receive the widest portion of the tang 38, but narrows quickly to be narrower than the width of the body 36 of the handle 34.

As best shown in FIGS. 3 and 6, the proximal end of the upper portion 66 is undercut, i.e., tapers outward below the curved section 82 toward the sidewall 18 at about a 45° angle to form a slanting camming surface 86. The camming surface 86 extends into the proximal end of the lower portion 68. The width of the lower portion 68 along its length will now be described.

From the distal wall 76 to a point which is distal to the shoulder 70, the width of the lower portion 68 is constant and is spaced from the left member 62 the distance $D_1$ shown in FIG. 4. However, at a point distal to the shoulder 70, the side 80 of the lower portion 68 angles outward at about a 45° angle toward the proximal end of the container 12 to form an edge 88. The edge 88 extends outward about ⅔ the width of the member 64 and then curves convexly in a section 90 which is concentric with the section 82 until merging with the sidewall 18. In similar fashion, the left member 62 has a left edge 88' and a curving section 90'.

The effect of the edges 88, 88' and the curving sections 90, 90' is to create a lower proximal portion of the channel 66 which is wider than any other portion. In this lower proximal portion, channel 66 is wide enough to accommodate the width of the body 36 and the handle 34. Importantly, this wider portion of the channel does not narrow back down to the width $D_1$ until a point distal to the shoulders 70, 70' as will become clear with the description of the method of use.

Moreover, the importance of the camming surfaces 86, 86' which form the boundary between the wide upper proximal opening of the channel 66 and the even wider lower proximal portion of the channel 66 will also be understood from the discussion below.

Referring to FIG. 1, in order to insert the handle 34 into the unit 10, the handle 34 is held in front of and somewhat above the unit 10 with the cutting portion 52 of the blade 32 directed toward the left member 62. Referring to FIGS. 7-8, in order to remove the blade 32, the handle 34 is pushed distally so that the tang 38 is positioned between the members 62, 64. This is possible since the distance $D_1$ (shown in FIG. 4) is larger than the tang 38. However, because $D_1$ is smaller than the width of the blade 32, the blade 32 will remain above the blade receiving surfaces 70, 70' with the heel of the blade 54 resting against the surfaces of the projections 72, 72'. The wedge shaped proximal portion 26 of the top 24 serves to guide the handle 34 and the blade 32 into this position.

The tang 38 is pushed distally between the members 62, 64 until the curvature of the sections 82, 82' matches the curvature of the left and right curved sides 35, 37 of the tang 38. In this position, shown in FIG. 7, the heel 54 of the blade 32 rests against the surfaces of the projections 72, 72' and the back edge 56 of the blade 32 is proximal to the shoulder 74, 74'. Moreover, as most clearly shown in FIG. 8, the body 36 is resting against the top of the camming surface 86. The operator will feel some resistance to further distal movement of the handle 34 because the channel 66 quickly narrows to the width $D_1$ which is narrower than the body 36 of the handle 34.

Referring to FIGS. 9-10, as the operator continues to push the handle 34 distally, the body 36 will be cammed downward along the camming surfaces 86, 86'. The camming surfaces 86, 86' therefore naturally direct the handle 34 into the lower proximal portion of the channel 66. In this portion, the channel 66 has a width which is sufficiently wide to accommodate the body 36 of the handle 34. The channel 66 in this widened area is long enough to permit the handle 34 to move distally until the heel 54 clears the shoulder 74, 74' of the projections 72, 72'. When this happens, the entire blade 32 will snap down to rest against the blade-receiving surfaces 70, 70'.

In this position, shown clearly in FIG. 9, the back edge 56 of the blade 32 abuts the complimentary angle of the shoulder 74, and the shorter lateral edge 58 of the blade 32 abuts the complimentary angle of the shoulder 74'.

It will now be understood that the upright edges 88, 88' must be distally offset from the proximal ends of the members 62, 64, a distance greater than the offset of the shoulders 74, 74' to permit the heel 54 of the blade 32 to abut the shoulders 74, 74'. If this were not true, the upright edges 88, 88' would stop further distal movement of the handle 34 before the blade 32 was able to clear the shoulders 74, 74'.

As the handle 34 is cammed downward, the heel 54 of the blade 32, which is held from further downward movement by the blade-receiving surfaces 70, 70', is pried over the tang 38. It will also be understood that the depth of the channel 66 must be sufficient to receive the tang 38 to permit the handle 34 to be cammed downward far enough to pry the heel 54 over the tang 38.

Once the heel 54 of the blade 32 is disengaged from the tang 38, the handle 34 is pulled longitudinally out of the unit 10. The blade 32 is prevented from following the handle 34 by the shoulders 74, 74' which abut the heel 54 of the blade 32. As best shown in FIG. 10, the wedge shaped proximal portion 26 of the top 24 serves as a guard to prevent the blade from rebounding off the surfaces 70, 70' out of the container 12.

Once removed, the blade 32 will slide into the cavity 22. The flange 78 of the distal wall 76 helps prevent removed blades from falling back out of the container 12 between the top 24 and the blade receiving surfaces 70, 70'. Advantageously, the container 12 is made of a transparent material so that hospital personnel can visually inspect and/or count removed blades in the cavity 22.

The blade remover provides for the safe, efficient removal of surgical blades without the operator having to contact the blades. The unit 10 has only two members which not only pry the heel of the blade over the tang, but also hold the blade while the handle is slidably removed from the the device. The method of use is particularly foolproof requiring little operator dexterity. The operator need only insert the handle into the unit from above and continue pushing distally until the handle is cammed downward along the camming surfaces and the heel of the blade clears the shoulders 74, 74' and then pull the handle out of the unit.

Furthermore, the unit can be placed in, and used in conjunction with many different types of containers, some of which will be exemplified in the following discussion with reference to FIGS. 11–18.

Referring to FIG. 11, a container 100 substantially identical to the container 12 having the remover unit 10 is shown. The container 100 is mounted to the side of a hinged box 104, having a mutually-hinged cover 106 and a base 108, which can be used to encapsulate various types of surgical instruments. Specifically, the container 100, which is of a length equal to the box 104, is fastened to the side of the base 108 by any suitable means, such as a protruding lug, which would snap into an aperture in the base 108.

Figure 12:
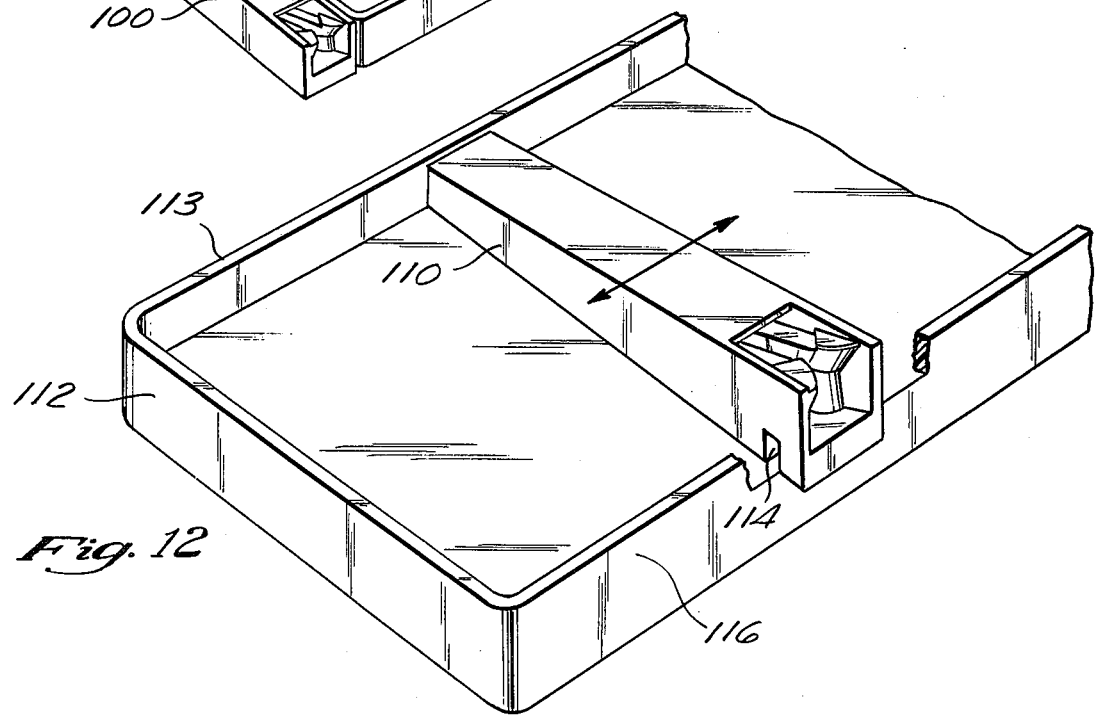
FIG. 12 is a perspective view of a second alternate embodiment.

Referring the FIG. 12, a container 110 having the unit 10, is shown in a four-sided, rectangular base 112. In this embodiment, the distal end of the container 110 tapers downward to a height which is just less than the height of a backside 113 of the base 112. The proximal end of the container 110 has a groove 114 on its underside, which receives the front side 116 of the base 112, thereby, permitting it to slide along the base 112. It should be understood in this embodiment that the cavity within the container, although covered, has no bottom. In this embodiment, the container 110 is placed over that portion of the base 112 on which the operator desires to deposit a removed blade. As the blade is released from the handle, it slides down onto the base area. The container is then slid laterally across the base to the next area of deposit. In this manner, removed blades can be neatly and accurately deposited in a row, allowing for easy counting and identification.

Figure 13:
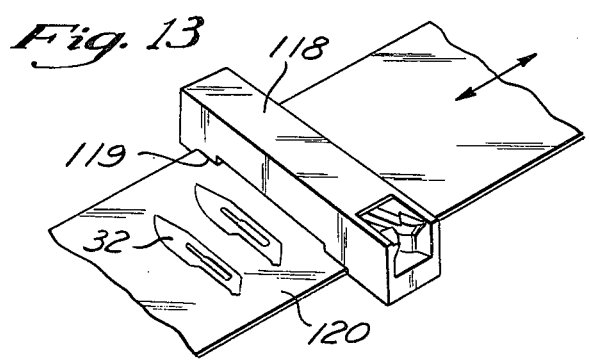
FIG. 13 is a perspective view of a third alternate embodiment.

Referring to FIG. 13, a container 118, having the unit 10, is shown. The cavity within the container 118 is covered, but has no bottom. The container 118 has a slot 119 extending through the bottom of its sidewalls in the region of the cavity to form a track which runs across the width of the container. The slot 119 receives a substrate 120 which can be slid laterally beneath the cavity. In use, the substrate 120 is moved after removing each blade so that the blades are deposited in a straight line as shown.

Figure 14:
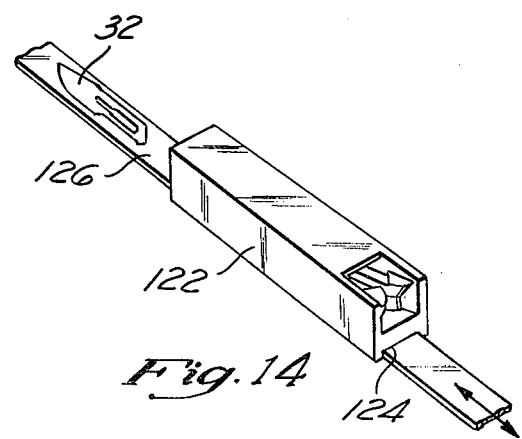
FIG. 14 is a perspective view of a fourth alternate embodiment.

Referring to FIG. 14, a container 122 having the unit 10 is shown. The cavity within the container 122 is covered, but has no bottom. The container 122 has a slot 124 located between the underside of the sidewalls running the length of the container 122. The slot 124 receives a substrate 126 which can be slid longitudinally beneath the cavity. It should be understood that the embodiment shown in FIG. 14 is very similar to that shown in FIG. 13, except that the substrate in FIG. 14 slides longitudinally beneath the cavity, across the length of the container, instead of sliding laterally beneath the cavity across the width of the container.

A further embodiment is shown in FIGS. 15–17. As shown most clearly in FIG. 17, a container 128 having the unit 10, is mounted by any suitable manner in a radial orientation to the top surface of a circular top 130. The top 130 has a centrally-located mounting post 132. A circular base 136 has a centrally-located circular post guide 133 having a central aperture 134. As best shown in FIGS. 15 and 16, the base 136 has a plurality of radially extending partitions 138, which divide the base into a multitude of wedge-shaped sections, shown generally as 140. Each of the sections 140 is large enough to accommodate at least one surgical blade. In order to mate the top 130 and the base 136, the post 132 is mounted within the aperture 134 of the post guide 133 so that the top 130 and the base 136 are mutually rotatable.

It should be understood that not only is the cavity within the container 128 bottomless, but the top 130 also has an opening located below the cavity. Thus, when a blade is removed from its handle, it will slide off the unit 10 down through the top 130 and into one of the sections 140. Before the next blade is removed, the operator will rotate the top 130 with respect to the base 136 so that an adjacent empty section will be positioned beneath the cavity. In this manner, each of the sections 140 will sequentially receive a removed blade, as clearly shown in FIG. 16. The top 130 is made of a transparent material so that the operator can visually inspect the contents of the sections 140 without having to remove the top. This embodiment allows for the easy identification and accountability of removed blades.

Referring to FIGS. 18–19, a final embodiment is shown having a container 138, which includes a unit 10. The cavity within the container 138 is bottomless. The container 138 sits within a trough-like base 142, which is shaped to fit over and around the lower portion of the container 138. At its distal end, the base 142 extends upward to about one-half the height of the container 138. The base 142 then tapers downward across the length of the container 138 ending in a proximal end which curves upward over the lower-most portion of the proximal end of the container 138. The base 142 serves to enclose the bottom of the cavity within the container 138. When the container 138 is filled with blades, the base 142 can be easily removed, and the blades disposed. After the base 142 is replaced, the container 138 is then emptied and ready for a multitude of additional uses.

I claim:

1. A device for removing a blade having an opening therethrough from a tang of a blade handle, said tang extending upwardly through said opening to mount said blade on said tang comprising:

two members spaced to form a channel, said members having distal and proximal ends and upper and lower portions, each of said upper portions having a blade receiving surface mutually spaced a distance greater than the width of the tang and less than the width of the blade;

the proximal ends of each of said upper portions having an upwardly extending projection to form a shoulder for abutting the heel of the blade;

each of said members having a camming surface between its proximal upper portion and proximal lower portion, said camming surface directing the handle between said lower portions as the handle is pushed distally while the blade rests against said blade receiving surfaces to pry the heel of the blade over the tang;

the proximal ends of said lower portion being mutually spaced a distance sufficient to permit said handle to be pushed distally between said members until the heel of said blade abuts said shoulders, said shoulders preventing said blade from moving with the handle as its is removed from the blade by pulling it longitudinally relative to the blade.

2. A device for removing a surgical blade from a tang of a blade handle comprising:

two spaced members each having blade receiving surfaces, said members being complimentary contoured to form a channel having a narrow portion and a wide portion;

said members having means for holding said blade to prevent the blade from moving with the handle when the handle is removed from the device;

said narrow portion of the channel being wider than the tang but narrower than the blade to permit the blade to rest against said blade receiving surfaces and to permit the blade to be pried over the tang when the handle is moved away from said surfaces;

said wide portion of the channel sized to permit the handle to enter the channel between the members sufficiently that the heel of the blade can engage said holding means.

3. A device for removing a blade having an opening therethrough from a tang of a blade handle comprising:

two members having distal and proximal ends spaced to form a channel, said members having upper surfaces which are suitable for supporting a surgical blade, each of said surfaces having means for abutting a heel of said blade;

said channel having first and second portions, said first portion being located between the distal ends of said members and of a width greater than the width of the tang but less than the width of the blade, said second portion being located between the proximal ends of said members and of a width sufficient to permit the handle to be pushed distally between the members beyond said abutting means so that when the handle is removed from the device, the abutting means abuts the heel of the blade to prevent the blade from moving with the handle.

4. A device for removing a blade from a tang of a blade handle comprising:

two members each having proximal and distal ends spaced to form a channel;

said members having means for supporting the blade spaced less than the width of the blade and greater than the width of the tang;

said members having means for holding the blade;

each member having a camming surface located between an upper and lower proximal end which is traversed by the handle as it is pushed toward the distal ends of the members while the blade rests against the blade supporting means to release the heel of the blade from the tang;

said members being spaced between their lower proximal ends a distance sufficient to permit the handle to be pushed between the members until the blade engages said holding means.

5. A device for removing a blade from a tang of a blade handle comprising:

two spaced members each having blade receiving surfaces, said surfaces being spaced a distance greater than the tang but less than the width of the blade, to permit the blade to rest against the surfaces and be pried over the tang when the handle is moved away from the surfaces;

each member having means for holding the heel of the blade when the heel is pried over the tang;

a portion of the members being spaced a distance sufficient to permit the handle to be pushed far enough distally that the heel of the blade engages the holding means to prevent the blade from moving with the handle when the handle is removed from the device.

* * * * *